(12) United States Patent
Wouters et al.

(10) Patent No.: US 9,778,192 B2
(45) Date of Patent: Oct. 3, 2017

(54) OBJECT CARRIER, SYSTEM AND METHOD FOR BACK LIGHT INSPECTION

(71) Applicant: KLA-Tencor Corporation, Milpitas, CA (US)

(72) Inventors: Christophe Wouters, Balen (BE); Steven Boeykens, Boeykens (BE); Carl Smets, Haasrode (BE)

(73) Assignee: KLA-Tencor Corporation, Milpitas, CA (US)

( * ) Notice: Subject to any disclaimer, the term of this patent is extended or adjusted under 35 U.S.C. 154(b) by 119 days.

(21) Appl. No.: 14/632,486

(22) Filed: Feb. 26, 2015

(65) Prior Publication Data

US 2015/0168304 A1 Jun. 18, 2015

Related U.S. Application Data

(63) Continuation of application No. PCT/US2013/056627, filed on Aug. 26, 2013.

(Continued)

(51) Int. Cl.
| | |
|---|---|
| *G01N 21/00* | (2006.01) |
| *H04N 7/18* | (2006.01) |
| *G01N 21/64* | (2006.01) |
| *G01N 21/88* | (2006.01) |
| *G01N 21/95* | (2006.01) |
| *G01N 21/958* | (2006.01) |

(52) U.S. Cl.
CPC ..... *G01N 21/6489* (2013.01); *G01N 21/8806* (2013.01); *G01N 21/9501* (2013.01); *G01N 21/958* (2013.01); *G01N 2201/02* (2013.01); *G01N 2201/061* (2013.01); *G01N 2201/062* (2013.01); *G01N 2201/06113* (2013.01); *G01N 2201/06193* (2013.01)

(58) Field of Classification Search
CPC .......... G01N 21/6489; G01N 21/8806; G01N 21/9501; G01N 21/958; G01N 2201/061
USPC ...................................... 250/458.1
See application file for complete search history.

(56) References Cited

U.S. PATENT DOCUMENTS

| | | | |
|---|---|---|---|
| 7,092,082 B1 | 8/2006 | Dardzinski | |
| 7,221,444 B1 * | 5/2007 | Zhao | G01N 21/8806 356/237.1 |

(Continued)

FOREIGN PATENT DOCUMENTS

| | | |
|---|---|---|
| JP | 2002251169 A | 9/2002 |
| JP | 2004294365 A | 10/2004 |
| KR | 1020060000989 A | 1/2006 |

*Primary Examiner* — Sunghee Y Gray
(74) *Attorney, Agent, or Firm* — Simpson & Simpson, PLLC

(57) ABSTRACT

An object carrier, a system and a method is disclosed for the back light inspection of transparent or semitransparent objects. The carrier has a carrier base layer with photo luminescent properties which carries the transparent or semitransparent object on top of the layer. The transparent or semitransparent object could be a wafer and the object carrier could be a wafer chuck. At least one light source being arranged above the object carrier such that excitation light emitted from the at least one light source is directed through the transparent or semitransparent object to the layer with photo luminescent properties. The light returned from the layer with photo luminescent properties is collected by an objective and registered by a sensor.

20 Claims, 5 Drawing Sheets

Related U.S. Application Data

(60) Provisional application No. 61/693,727, filed on Aug. 27, 2012.

(56) References Cited

U.S. PATENT DOCUMENTS

| | | | |
|---|---|---|---|
| 8,068,661 B2 | 11/2011 | Onushkin et al. | |
| 2009/0206287 A1* | 8/2009 | Trupke | G01N 21/6489 250/582 |
| 2010/0297562 A1 | 11/2010 | Shibazaki | |
| 2011/0117681 A1* | 5/2011 | Bardos | C23C 16/52 438/7 |
| 2013/0015370 A1* | 1/2013 | Damaskinos | G01N 21/6452 250/459.1 |

\* cited by examiner

OBJECT CARRIER, SYSTEM AND METHOD FOR BACK LIGHT INSPECTION

CROSS-REFERENCE TO RELATED APPLICATIONS

This application is filed under 35 U.S.C. §111(a) and §365(c) as a continuation of International Patent Application No. PCT/US2013/056627, filed on Aug. 26, 2013, which application claims the benefit of U.S. Provisional Patent Application No. 61/693,727, filed on Aug. 27, 2012, which applications are incorporated herein by reference in their entireties.

FIELD OF THE INVENTION

The present invention relates generally to an object carrier for back light inspection of transparent or semitransparent objects.

The invention also relates generally to a system for back light inspection of transparent or semitransparent objects.

Additionally, the present invention relates to a method for back light inspection.

BACKGROUND OF THE INVENTION

Back light illumination is typically used to detect defects in non-transparent parts of transparent wafers, e.g., finger cuts in LED wafers.

FIG. 1 shows a schematic representation of a typical system 1 for generating back light inspection of transparent or semitransparent objects 2 according to a first concept. Light source 6 is part of object carrier 10 for the transparent or semitransparent object 2. Light source 6 is covered with transparent plate 11 so that light 5 from light source 6 reaches object 2. Only a portion of light 7 of light source 6 reaches optical unit 8. From there, a portion of light 7 reaches sensor 12. Light source 6 is mounted on stage 9, which is able to position object 2 with respect to optical arrangement 8. The size of light source 6 needs to be at least equal to the size of the transparent or semitransparent object 2.

Due to heat dissipation and power requirements, the output of light source 6 and the inspection speed is limited. Since the size of the transparent or semitransparent objects 2 increases, the heat dissipation of light source 6 increases too. Furthermore, as shown in FIG. 1, the illumination is insufficient, since most of light 5 is not captured by optical arrangement 8.

Another problem is that a part of the transparent or semitransparent object 2 is illuminated with a different part of light source 6. This will result in different image brightness for different parts of object 2. Further, the movement of light source 6 and the transparent or semitransparent object 2 is limited due to the cabling (not shown) of the light source 6.

A schematic representation of another typical arrangement for back light inspection is shown in FIG. 2. Here, light source 6 is not part of object carrier 10. In this case, light source 6 for back light illumination is fixed light source 6. The transparent or semitransparent object 2 moves between light source 6 for back light illumination and optical unit 8. Stage 9 and carrier 10 need to be designed in such a way that movement is not blocked by fixed light source 6. The size of the light source 6 needs to be at least equal to the size of the largest field of view of the optical unit 8.

The design of stage 9 is complex in order to enable movement of carrier 10 and the transparent or semitransparent object 2 around light source 6. Carrier 10 object 2 cannot be supported at the center since this space is taken by light source 6. The associated bending of carrier 10 and object 2 will lead to different focus positions at different locations on the transparent or semitransparent object 2 and image distortion in general.

SUMMARY OF THE INVENTION

The present invention comprises an object carrier for back light inspection of a transparent or semitransparent object, having a carrier base, and, a first layer with photo luminescent properties for carrying the transparent or semitransparent object on top of the layer.

The present invention also comprises a system for back light inspection of a transparent or semitransparent object having an object carrier with a carrier base and a layer with photo luminescent properties, a first light source arranged above the object carrier such that first excitation light emitted from the first light source is directed through the transparent or semitransparent object to the layer with photo luminescent properties, an optical unit adapted to capture emission light emitted from the layer with photo luminescent properties and traveled through the transparent or semitransparent object, and a sensor for registering the emission light captured by the optical unit.

The present invention also comprises a system for back light inspection of a transparent or semitransparent object, comprising an object carrier with a carrier base and a layer with photo luminescent properties, a microscope objective defining a first beam path, at least one first light source, wherein illumination light, with an excitation waveband of $\lambda_{ex} \pm \Delta\lambda_{ex}$, from the at least one first light source is directed via the first beam path of the microscope objective onto the object carrier such that the illumination light emitted from the at least one first light source passes through the transparent or semitransparent object to the layer with photo luminescent properties, and, a sensor is arranged such that only light with an emission waveband $\lambda_{em} \pm \Delta\lambda_{em}$ reaches the sensor, wherein the light travels through the transparent or semitransparent object and is captured with the microscope objective.

The present invention also comprises a system for back light inspection of transparent or semitransparent objects having an object carrier with a carrier base and a layer with photo luminescent properties, a microscope objective, defining a first beam path, at least one first light source, wherein illumination light, with an excitation waveband of $\lambda_{ex} \pm \Delta\lambda_{ex}$, defines an illumination beam with a second beam path so that light with the excitation waveband of $\lambda_{ex} \pm \Delta\lambda_{ex}$ is directed to the transparent or semitransparent object along the second beam path which is different from the first beam path of the microscope objective, and, a sensor is arranged such that only light with an emission waveband $\lambda_{em} \pm \Delta\lambda_{em}$ reaches the sensor, wherein the light travels through the transparent or semitransparent object and is captured with the microscope objective.

The present invention also comprises a system for back light inspection of a transparent or semitransparent object, comprising an object carrier, a carrier base and a bulk material layer with photo luminescent properties which is coated at a side of the carrier base with a reflective coating, a microscope objective, defining an illumination beam path, at least one first light source, wherein illumination light, with an excitation waveband of $\lambda_{ex} \pm \Delta\lambda_{ex}$, from the at least one light source is directed via the illumination beam path of the microscope objective onto the object carrier such that illumination light emitted from the at least one light source passes through the transparent or semitransparent object to the layer with photo luminescent properties, and, a sensor is arranged such that only light with an emission waveband $\lambda_{em} \pm \Delta\lambda_{em}$ reaches the sensor, wherein the light travels through the transparent or semitransparent object and is captured with the microscope objective.

The present invention also comprises a method having the steps of directing at least one illumination light beam with an excitation waveband of $\lambda_{ex} \pm \Delta\lambda_{ex}$ through a transparent or semitransparent object onto a layer with photo luminescent properties, capturing light emitted with an emission waveband of $\lambda_{em} \pm \Delta\lambda_{em}$ from the layer with photo luminescent properties and traveled through the transparent or semitransparent object, and, generating an image from the light with the emission waveband $\lambda_{em} \pm \Delta\lambda_{em}$, wherein $\lambda_{em} \pm \Delta\lambda_{em} \neq \lambda_{ex} \pm \Delta\lambda_{ex}$.

In an example embodiment, the object carrier can have as well the form of a wafer chuck and the transparent or semitransparent object is a transparent or semitransparent wafer. The layer with photo luminescent properties of the object carrier is composed of a bulk layer with photo luminescent properties that can have a reflective coating at the side of layer which faces the carrier base. The excitation illumination forces the layer with photo luminescent properties to emit light in a different wave length. According to a preferred embodiment, the bulk layer with photo luminescent properties is a porous layer. The reflective coating on one side of the bulk layer can be an aluminum coating.

A vacuum means, which is mounted to the porous bulk layer, insures that the transparent or semitransparent object is fixed to the object carrier or chuck. The vacuum is applied to the object through pores and micro holes of the bulk layer, respectively.

According to another embodiment of the invention the layer with photo luminescent properties is composed of a glass plate with a photo luminescent coating. The photo luminescent coating can be covered with a reflective coating while the reflective coating faces the carrier base. Preferably, the reflective coating is an aluminum coating and the photo luminescent coating is made of phosphor.

In this embodiment, also vacuum means is mounted to the glass plate so that a vacuum can be applied to the object trough micro holes or micro grooves of the glass plate.

A size and shape of the layer with photo luminescent properties are at least equal to a size and shape of the transparent or semitransparent object. Furthermore, the layer with photo luminescent properties has a plurality of pin lifting holes, wherein each pin in the pin lifting holes is made of the same photo luminescent material or material composition as the layer with photo luminescent properties.

The at least one light source of the system being arranged above the object carrier such that excitation light emitted from the at least one light source is directed through the transparent or semitransparent object to the layer with photo luminescent properties. The excitation waveband of $\lambda_{ex} \pm \Delta\lambda_{ex}$ can be generated by a light source that emits this waveband directly, or can be generated by a broadband emitting light source where a filter is applied to. The sensor (camera) is configured such that a registered image is defined by an emission waveband $\lambda_{em} \pm \Delta\lambda_{em}$ and wherein $\lambda_{em} \pm \Delta\lambda_{em} \neq \lambda_{ex} \pm \Delta\lambda_{ex}$. The layer with photo luminescent properties converts the excitation waveband of $\lambda_{ex} \pm \Delta\lambda_{ex}$ into the emission waveband $\lambda_{em} \pm \Delta\lambda_{em}$ where $\lambda_{em} > \lambda_{ex} \pm \Delta\lambda_{ex}$ or $\lambda_{em} < \lambda_{ex} \pm \Delta\lambda_{ex}$. At least one optical filter is arranged prior to the sensor, so that only light of the emission waveband $\lambda_{em} \pm \Delta\lambda_{em}$ reaches the sensor. According to a further embodiment, the sensor is insensitive to the excitation waveband of $\lambda_{ex} \pm \Delta\lambda_{ex}$ and sensitive to at least a portion of the emission waveband $\lambda_{em} \pm \Delta\lambda_{em}$.

The sensor can be configured in the form of an area scan camera, a line scan camera or a time delay integration line scan camera.

There are several possibilities to carry out the illumination of the transparent or semitransparent object and the layer with photo luminescent properties. Firstly, the excitation light emitted by the at least one light source travels through the optical unit to the layer with photo luminescent properties. Secondly, the excitation light emitted by the at least one light source travels outside the optical unit to the layer with photo luminescent properties. Thirdly, the excitation light emitted by the at least one first light source travels through the optical unit to the layer with photo luminescent properties and the excitation light emitted by the at least one second light source travels outside the optical unit to the layer with photo luminescent properties.

The at least one first and/or second light source are configured as a lamp or a combination of lamps, as an LED or a combination of LEDs or as a laser or a combination of lasers.

The optical unit of the system has at least one microscope objective and at least one optical filter so that only light with an emission waveband of $\lambda_{em} \pm \Delta\lambda_{em}$ from the layer with photo luminescent properties reaches the sensor. The microscope objective defines a beam path. A dichroic beam splitter is arranged in the optical unit such that light from the at least one first light source with the excitation waveband of $\lambda_{ex} \pm \Delta\lambda_{ex}$ is coupled into the beam path of the microscope objective. According to a different embodiment, the microscope objective defines a beam path and the light from the at least one further light source with the excitation waveband of $\lambda_{ex} \pm \Delta\lambda_{ex}$ defines an illumination beam path which is different from the beam path of the microscope objective. Combinations of the above described embodiment are possible as well.

An improvement over typical systems is that the light source is not located in the chuck base or object carrier base. Therefore no heat generation takes place below the wafer or the transparent or semitransparent object to be inspected. Accordingly, stronger light sources can be used without affecting the wafer or the transparent or semitransparent object. This leads to higher inspection speeds and an increased throughput. Furthermore, only the inspection spot of the wafer or the transparent or semitransparent object is illuminated which leads to higher efficiency. The homogeneity is improved because only one light source is used instead of an array of different LED's. In case bigger wafer sizes need to be inspected with back light there is only the requirement for a bigger chuck. The light source can stay the same. In case of the typical design, the number of LED's needs to be increased too. A vacuum can be applied through pores or micro holes/grooves of the object carrier, which do not affect the image. Vacuum holes in the typical design would affect image quality.

Embodiments of the system according to the present invention allow for illuminating at least partially transparent or semi-transparent (non-opaque) objects such as semiconductor wafers from one side in order to capture the transmitted light from the other side of the object. The light source illuminating the object, the object placed in front of layer with photo luminescent properties. A microscope optic and a camera capture the inspection image.

The present invention allows wafer manufacturers to increase wafer quality and yield. Back light inspection makes defects visible which are otherwise not detectable. The wafer size does not influence the inspection speed which allows the concept to grow together with the customers wafer size.

These and other objects, advantages and features of the present invention will be better appreciated by those having ordinary skill in the art in view of the following detailed description of the invention in view of the drawings.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
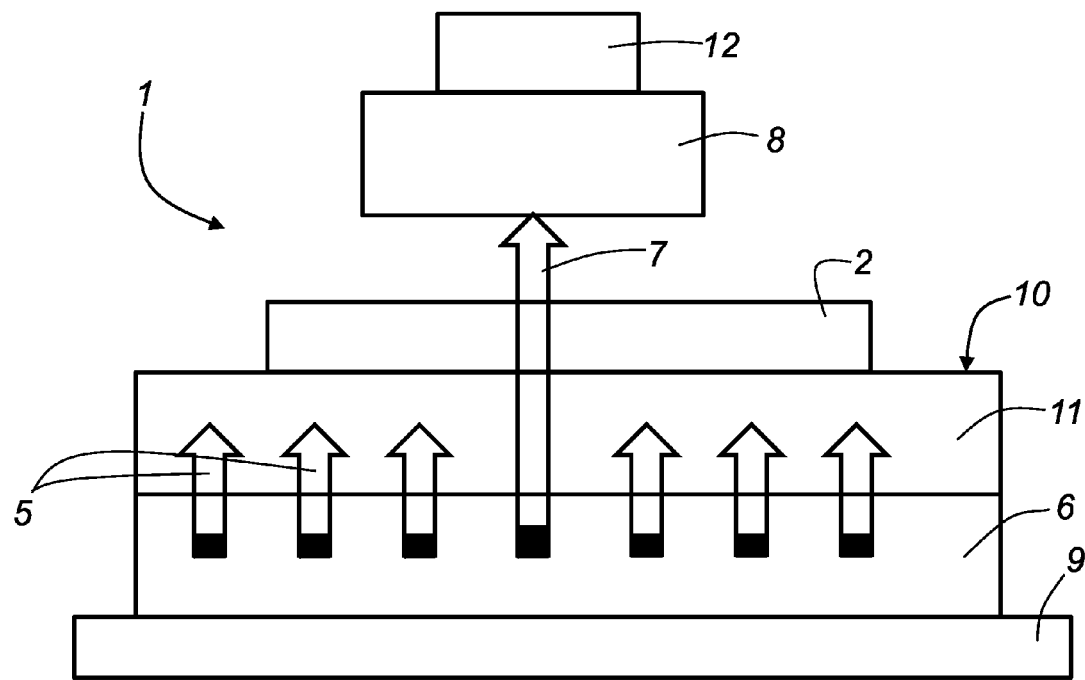
FIG. 1 is a schematic representation of a prior art arrangement for back light inspection.
Figure 2:
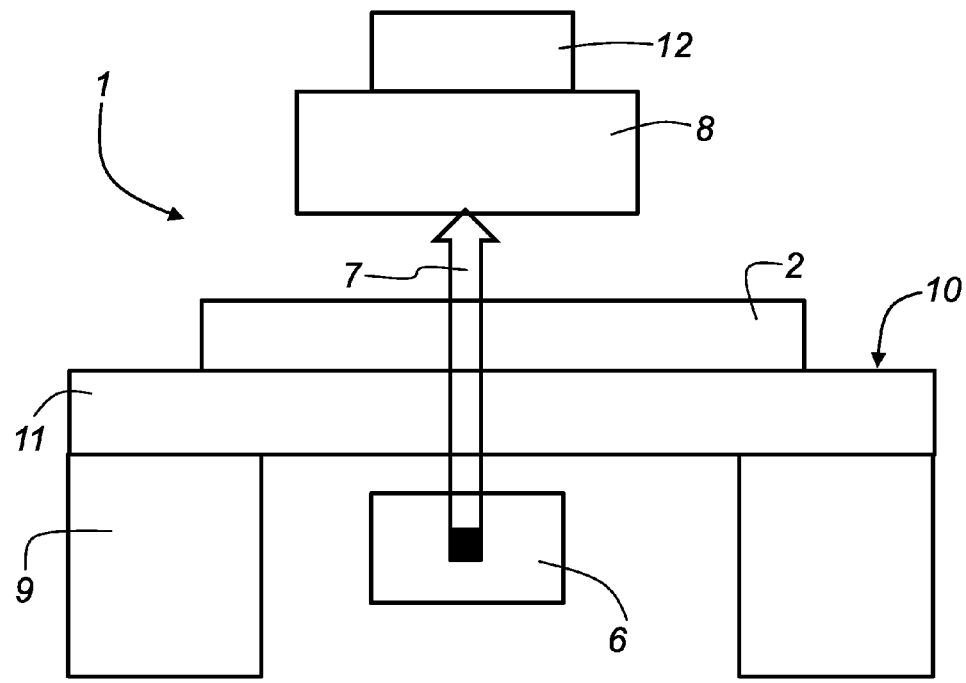
FIG. 2 is a schematic representation of another embodiment of a prior art arrangement for back light inspection.

In the drawings, identical reference characters are used for like elements of the present invention or elements of like function. For the sake of clarity, only those elements and reference characters which are of relevance to the shown aspects of the respective embodiment of the present invention are shown repeatedly.

While the present invention is described with respect to what is presently considered to be the preferred aspects, it is to be understood that the invention as claimed is not limited to the disclosed aspect. Also, it is to be understood that the invention is not limited in its application to the details of construction and the arrangement of the components set forth in the following description or illustrated in the drawings. The invention is applicable to other embodiments or of being practiced or carried out in various ways and is intended to include various modifications and equivalent arrangements within the spirit and scope of the appended claims.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

In the below description, an embodiment is an example or implementation of the invention. The various appearances of "one embodiment", "an embodiment", "certain embodiments" or "some embodiments" do not necessarily all refer to the same embodiments.

Figure 3:
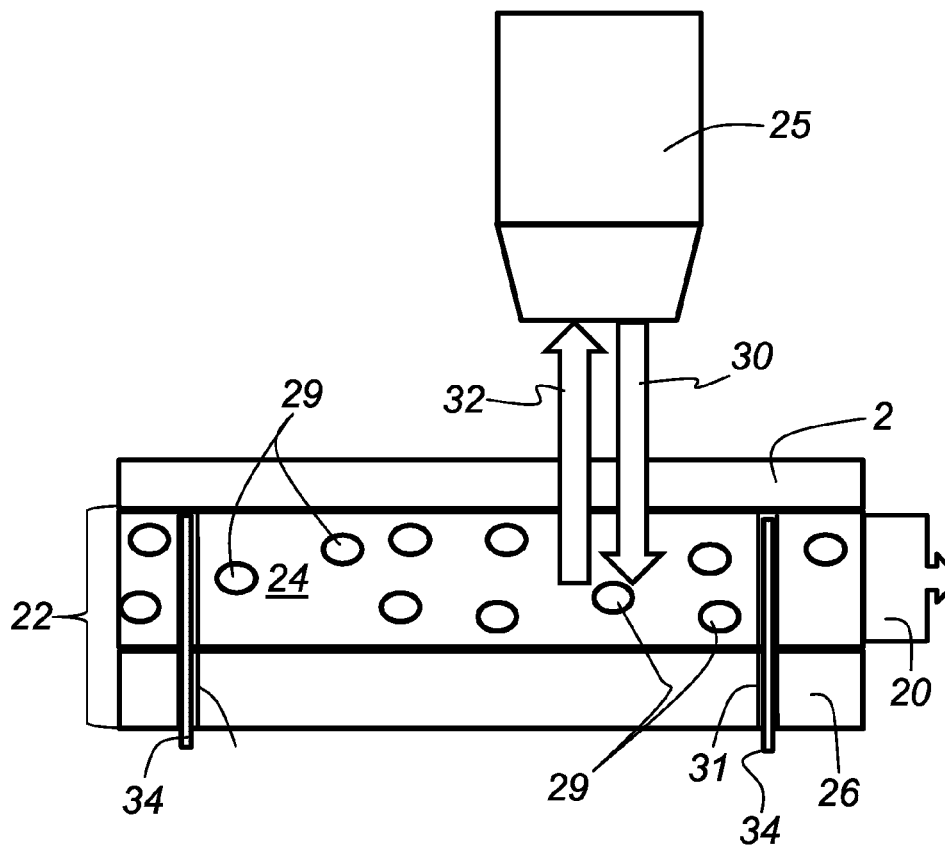
FIG. 3 is a schematic representation of an example embodiment of the present invention for the back light inspection of objects.

FIG. 3 is a schematic representation of one inventive embodiment for the back light inspection of transparent or semitransparent objects 2. Object 2 rests on layer 22 with photo luminescent properties. Layer 22 is composed of bulk layer 24, having the photo luminescent properties; with reflective coating 26 at the side of layer 22 which faces carrier base 18 (see FIGS. 6-8). Opposite to the object 2, objective lens 25 is arranged. Objective lens 25 can be a microscope objective. Excitation light 30 is emitted from the at least one light source (not shown) and directed via objective lens 25 to object 2. Excitation light 30 passes through object 2 and reaches bulk layer 24 with photo luminescent properties. In bulk layer 24, emission light 32 is generated which travels through object 2 and is captured by objective lens 25.

The embodiment shown in FIG. 3 has vacuum means 20, which is mounted to the porous bulk layer so that a vacuum is applied to the object through micro pores 29 of bulk layer 24. Applying a vacuum to object 2 via vacuum means 20 enables object 2 (wafer) to be in firm contact with layer 22 with photo luminescent properties. In order to facilitate the removal of object 2, layer 22 with photo luminescent properties has pin lifting holes 31 and lifting pins 34. The top of lifting pins 34 is made of the same photo luminescent material as layer 22 with photo luminescent properties to limit the disturbance of the image.

Figure 4:
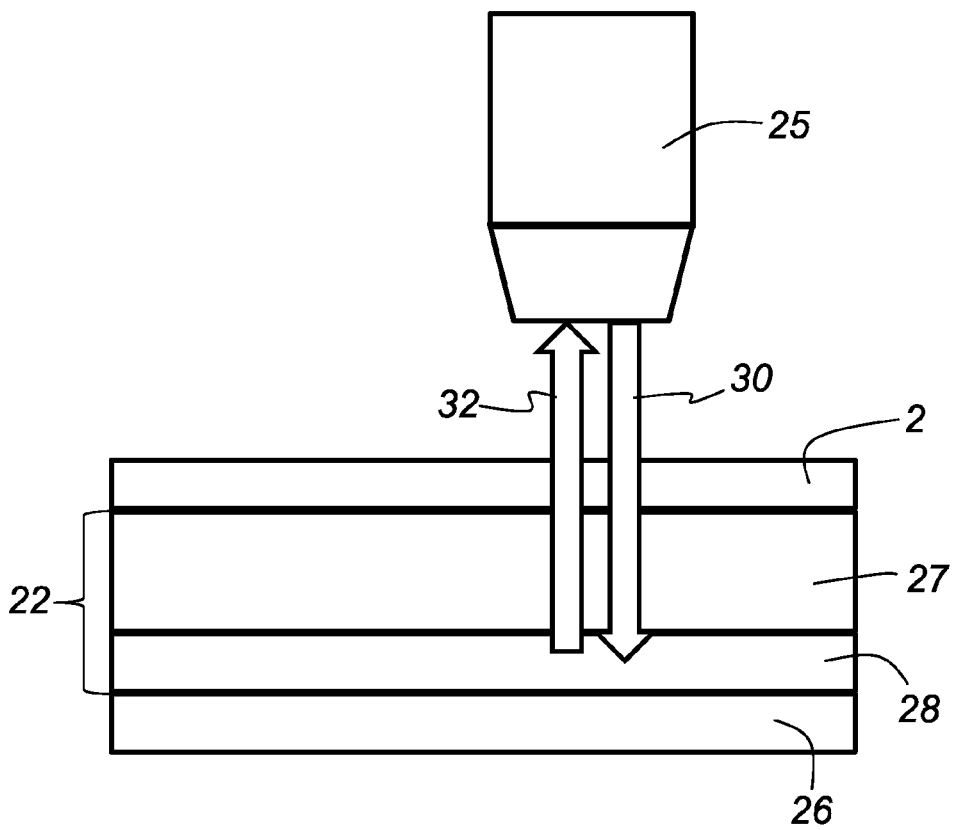
FIG. 4 is a schematic representation of an example embodiment of the present invention for the back light inspection of objects.

FIG. 4 shows a schematic representation of an example embodiment for the back light inspection of objects 2. Here layer 22 with photo luminescent properties is composed of glass plate 27 with photo luminescent coating 28. The material of photo luminescent coating 28 could be phosphor. Photo luminescent coating 28 is covered with reflective coating 26 on the coating which faces carrier base 18 (see FIGS. 6-8). In the example embodiments shown in FIGS. 3 and 4, reflective coating 26 is made of aluminum. Excitation light 30 is emitted from the at least one light source (not shown) and directed via objective lens 25 to object 2. Excitation light 30 passes through object 2, glass plate 27 and reaches photo luminescent coating 28. With luminescent coating 28, emission light 32 is generated which travels through glass plate 27 and object 2 and is captured by objective lens 25. In the instance that luminescent coating 28 is a phosphor coating, excitation light 30 covers a waveband from ultraviolet to blue and emission light 32 covers a waveband from green to red.

Figure 5:
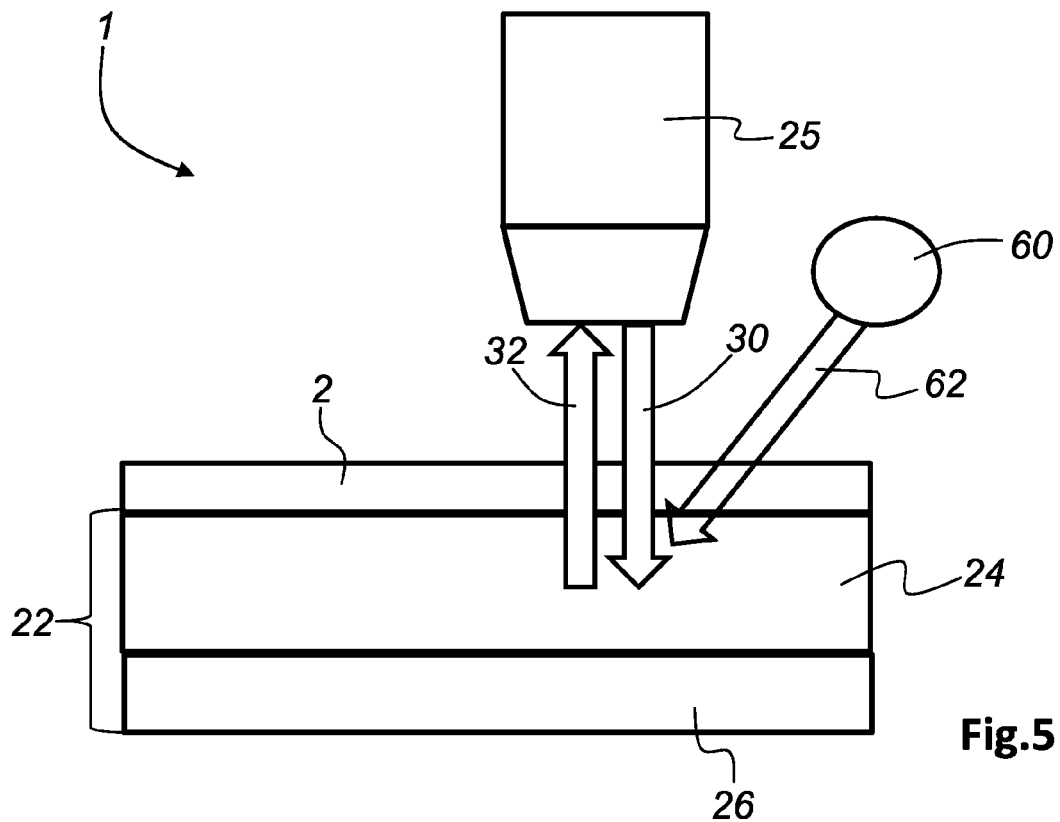
FIG. 5 is a schematic representation of an alternative for the illumination in order to achieve the back light illumination of transparent or semitransparent objects.

In FIG. 5, an additional illumination concept for layer 22 with photo luminescent properties is shown. Layer 22 with photo luminescent properties is identical with layer 22 shown in FIG. 3. Excitation light 30, having a waveband in the ultraviolet region, is emitted from the at least one light source (not shown) and directed via objective lens 25 to object 2. Excitation light 30 passes through object 2 and reaches bulk layer 24 with photo luminescent properties.

Additionally, at least one further light source 60 is provided, which directs its excitation light 62 in the green waveband and/or blue waveband through object 2 to bulk layer 24 with photo luminescent properties. In bulk layer 24, emission light 32 is generated which travels through object 2 and is captured by objective lens 25.

Figure 6:
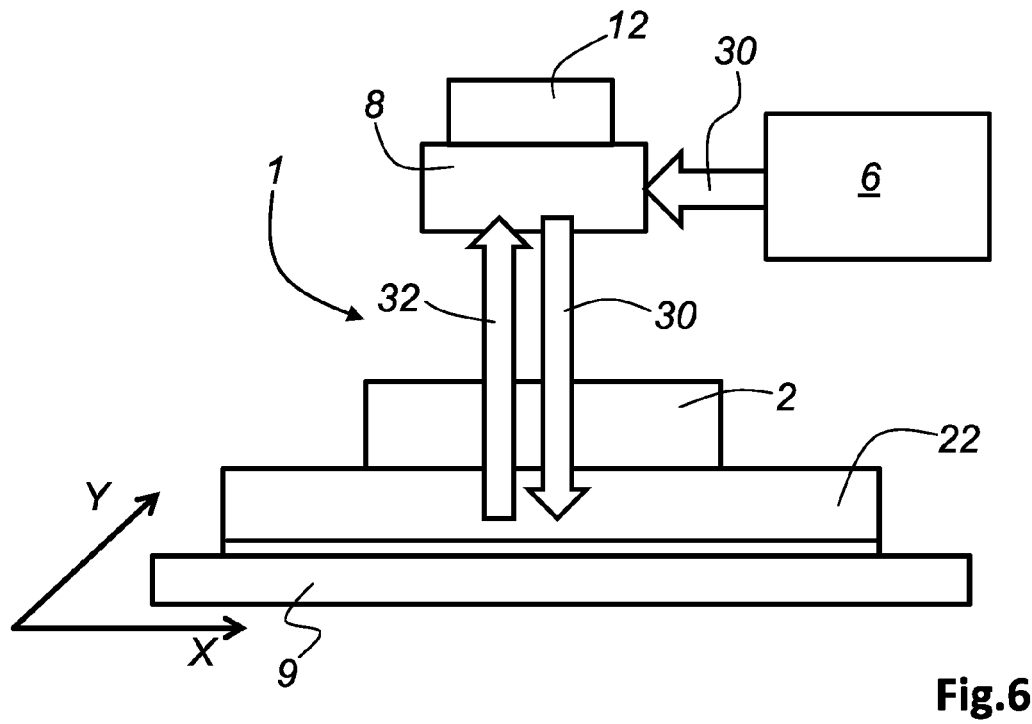
FIG. 6 is a schematic representation of a system for back light inspection of transparent or semitransparent objects.

FIG. 6 is a schematic representation of an example embodiment of system 1 for back light inspection of objects 2. Object 2 is positioned on stage 9 for moving object 2 along X-coordinate direction X and Y-coordinate direction Y. Stage 9 enables the positioning of various sections of object 2 in excitation light 30 emitted by the at least one light source 6. Excitation light 30 exits light source 6 and enters optical unit 8 and from optical unit 8 excitation light 30 reaches layer 22 via microscope objective 25 (see FIGS. 3-5) and object 2. Excitation light 30 reaches layer 22 with a waveband of $\lambda_{ex} \pm \Delta\lambda_{ex}$. From layer 22 with photo luminescent properties, light 32 with an emission waveband of $\lambda_{em} \pm \Delta\lambda_{em}$ reaches optical unit 8 and the associated sensor 12. Sensor 12 is configured such that a registered image is defined by an emission waveband $\lambda_{em} \pm \Delta\lambda_{em}$ and wherein $\lambda_{em} \pm \Delta\lambda_{em} \neq \lambda_{ex} \pm \Delta\lambda_{ex}$.

Figure 7:
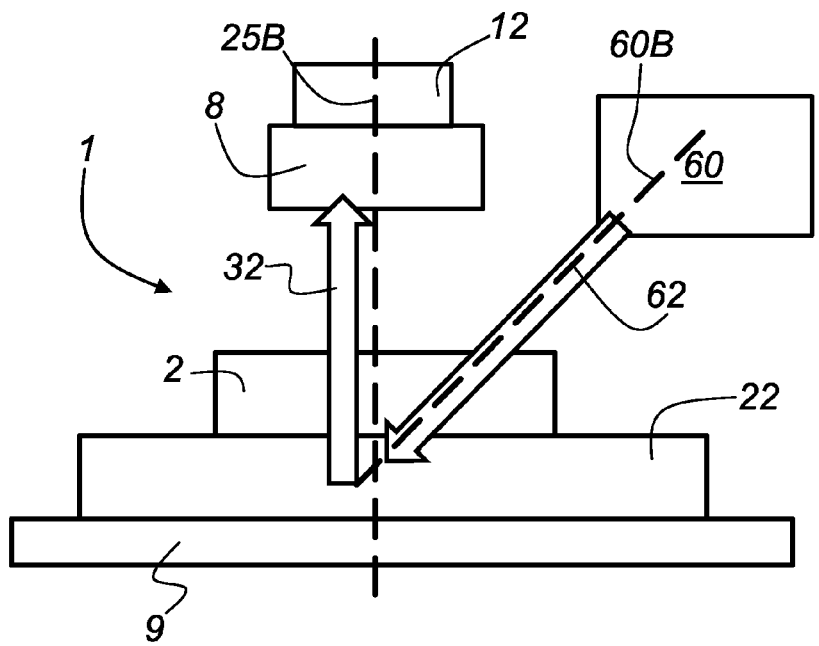
FIG. 7 is a schematic representation of another embodiment of the system for back light inspection.

A further embodiment of system 1 is shown in FIG. 7. Another light source 60 is arranged such that excitation light 62 emitted by light source 60 travels outside optical unit 8 via object 2 to layer 22 with photo luminescent properties. Microscope objective 25 of optical unit 8 defines beam path 25B and the light from the at least one further light source 60 with the excitation waveband $\lambda_{ex} \pm \Delta\lambda_{ex}$ defines illumination beam path 60B which is different from beam path 25B of microscope objective 25 (see FIGS. 3-5). Again, sensor 12 is configured such that a registered image is defined by an emission waveband $\lambda_{em} \pm \Delta\lambda_{em}$ of emission light 32 exiting layer 22 with photo luminescent properties through object 2 and wherein $\lambda_{em} \pm \Delta\lambda_{em} \neq \lambda_{ex} \pm \Delta\lambda_{ex}$. A combination of the embodiments shown in FIGS. 6 and 7 is possible as well. Here, light 30 from light source 6 is coupled into beam path 25B and light 62 from the at least one further light source 60 is coupled with the excitation waveband of $\lambda_{ex} \pm \Delta\lambda_{ex}$ in illumination beam path 60B which is different from beam path 25B.

Figure 8:
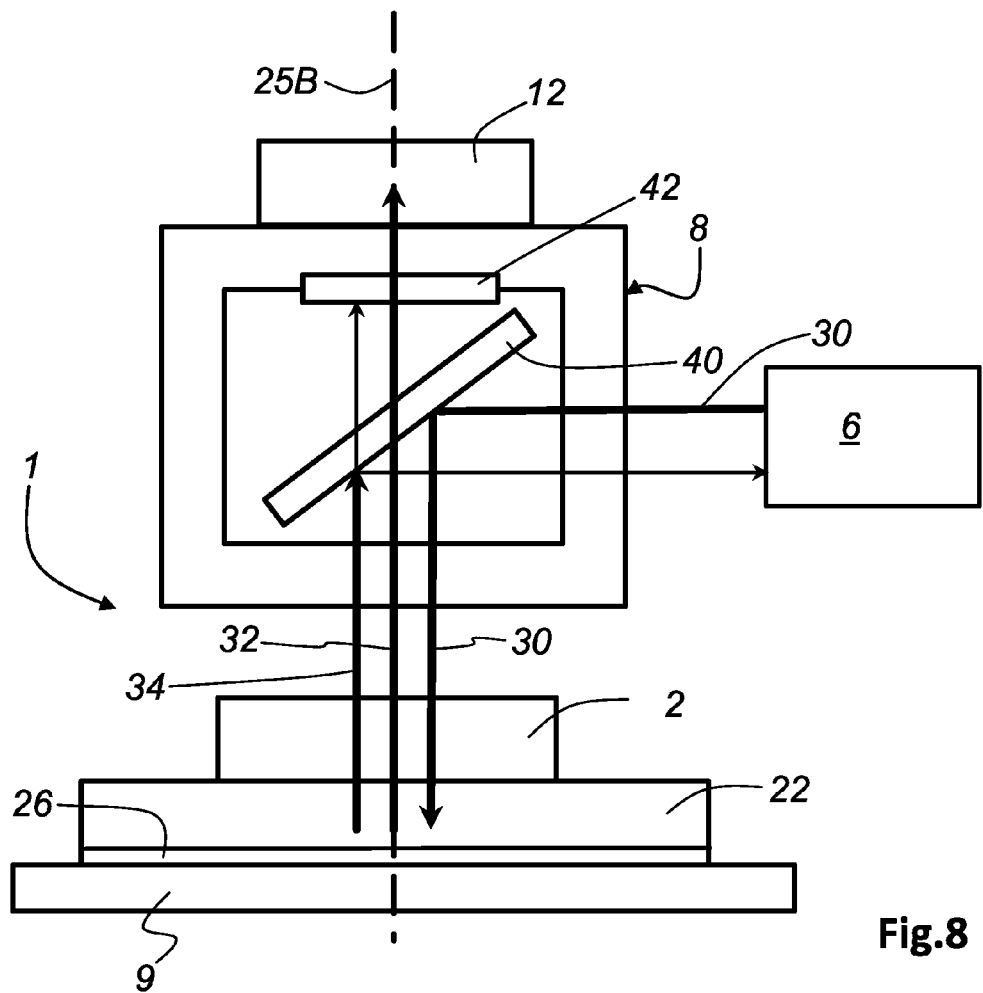
FIG. 8 is a schematic representation of an implementation of the system according to one embodiment of the invention; and, FIG. 9 is a schematic representation of an implementation of the system according to a further embodiment of the invention.

FIG. 8 is a schematic representation of an implementation of system 1 according to an example embodiment. Layer 22 with photo luminescent properties is on carrier base 26 and carrier base 26 is positioned on stage 9. Here, one light source 6 is arranged above object 2. Excitation light 30 emitted from light source 6 is directed through object 2 to layer 22 with photo luminescent properties. Again, microscope objective 25 (see FIGS. 3-5) defines beam path 25B. Dichroic beam splitter 40 is arranged in optical unit 8 such that light from light source 6 is coupled into beam path 25B with the excitation waveband of $\lambda_{ex} \pm \Delta\lambda_{ex}$. At least one optical filter 42 is arranged in front of sensor 12 so that only light 32 of the emission waveband $\lambda_{em} \pm \Delta\lambda_{em}$ reaches sensor 12. In an example embodiment, sensor 12 is insensitive to light 30 of the excitation waveband of $\lambda_{ex} \pm \Delta\lambda_{ex}$ and only sensitive to at least a portion of the emission waveband $\lambda_{em} \pm \Delta\lambda_{em}$.

Light 32 returning from layer 22 contains the emission waveband $\lambda_{em} \pm \Delta\lambda_{em}$ and light 34 returning from layer 22 also contains the excitation waveband $\lambda_{ex} \pm \Delta\lambda_{ex}$, wherein $\lambda_{em} \pm \Delta\lambda_{em} \neq \lambda_{ex} \pm \Delta\lambda_{ex}$. Dichroic beam splitter 40 lets a portion of light 34 with the excitation waveband $\lambda_{ex} \pm \Delta\lambda_{ex}$ pass and, as mentioned above, this portion is blocked by optical filter 42 so that it does not reach sensor 12. On the other hand, a portion of light 34 with the excitation waveband $\lambda_{ex} \pm \Delta\lambda_{ex}$ is reflected by dichroic beam splitter 40 back into light source 6.

In the case where light source 6 in FIG. 8 emits blue light with a wavelength of 460 nm, dichroic beam splitter 40 in optical unit 8 (microscope) has a cut on at the wavelength of 514 nm. Here, light 30 shines through object 2 (wafer) on layer 22 having photo luminescent properties. Layer 22 emits white light 32 which is sent to sensor 12 (camera) through dichroic beam splitter 40 and high pass filter 42, which has a cut on a wavelength of 514 nm.

Figure 9:
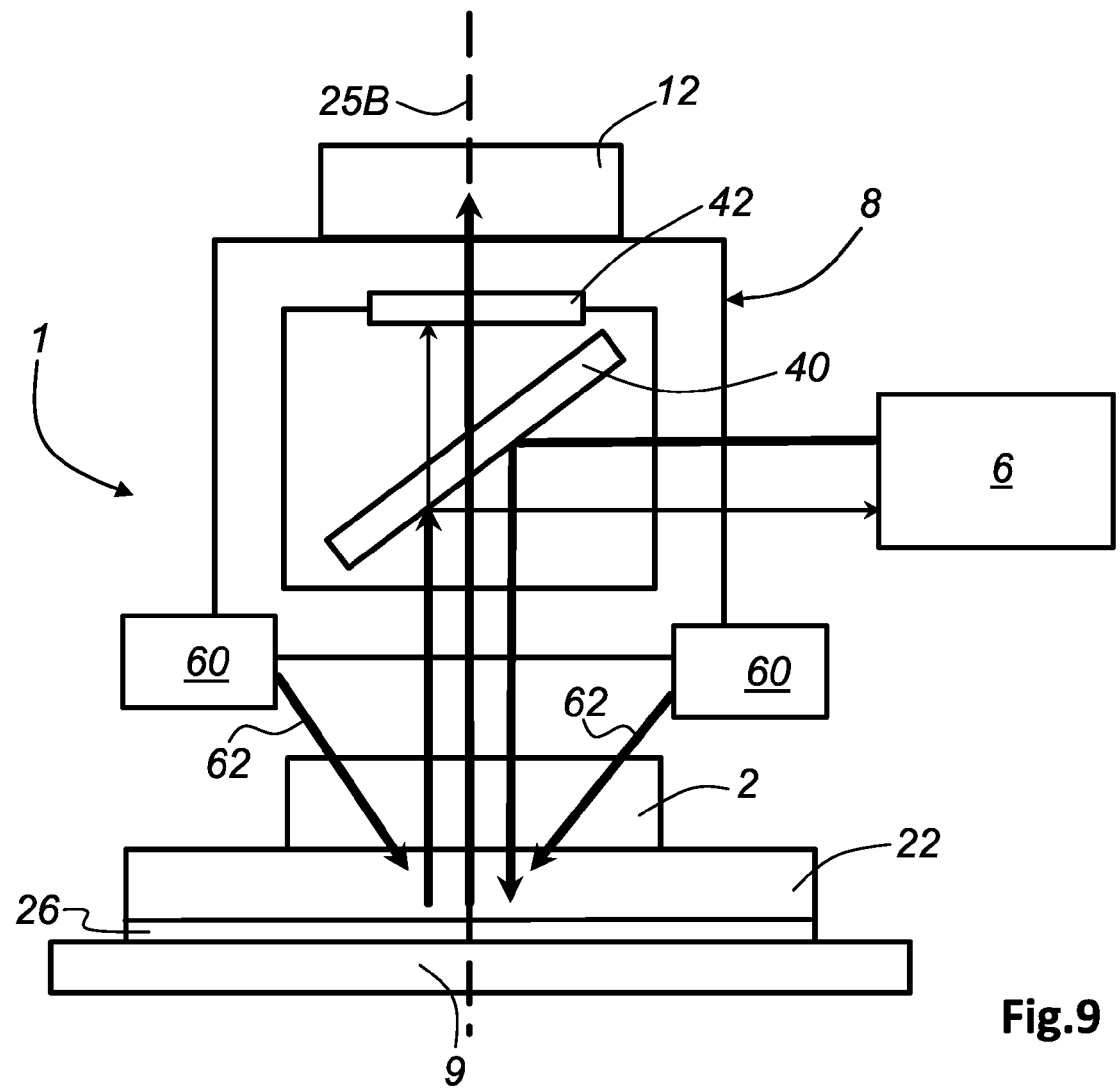

FIG. 9 is a schematic representation of an implementation of system 1 according to an example embodiment. Here, in addition to light source 6 (excitation light in the UV region), two further light sources 60 are provided. Light sources 60 are arranged such that excitation light 62 from the further light sources 60 travels outside optical unit 8 via object 2 to layer 22 having photo luminescent properties. The number of further light sources 60 shown in this embodiment should not be regarded as limiting the scope of the invention. It is clear for a person having ordinary skill in the art that the number of further light sources 60 can be selected according to the inspection requirements.

In the case where the further light source 60 is a ring light with an excitation light in the green light region, it might be worthwhile to use a different set of filters to have the range UV-green available as excitation wavelengths. The emission filter should only transmit the red. This will block the blue response from object 2.

The invention is not limited to those diagrams or to the corresponding descriptions. For example, flow need not move through each illustrated box or state, or in exactly the same order as illustrated and described.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention as claimed.

LIST OF REFERENCE CHARACTERS

1 System
2 Transparent or semitransparent object
4 Carrier
5 Light from light source
6 Light source
7 Portion of light
8 Optical unit
9 Stage
10 Object carrier, wafer chuck
12 Sensor
20 Vacuum means
22 Layer with photo luminescent properties
24 Bulk plate
25 Objective lens, microscope objective
25B Beam path
26 Reflective coating
27 Glass plate
28 Phosphor coating
29 Micro pores
30 Excitation light, illumination light
31 Lifting holes 32 Emission light
34 Lifting pins
40 Dichroic beam splitter
42 Optical filter
60 Further light source
60B Illumination beam path
62 Excitation light
X X-coordinate direction
Y Y-coordinate direction

What is claimed is:

1. A system for back light inspection of a transparent or semitransparent object, comprising:
an object carrier with a carrier base and a layer with photo luminescent properties wherein the transparent or semitransparent object rests on the layer with photo luminescent properties;
a first light source arranged above the object carrier such that first excitation light emitted from the first light source is directed through the transparent or semitransparent object to the layer with photo luminescent properties;
an optical unit adapted to capture emission light emitted from the layer with photo luminescent properties and traveled through the transparent or semitransparent object; and
a sensor for registering the emission light captured by the optical unit, wherein the sensor is an area scan camera or a line scan camera.

2. The system of claim 1, wherein the first excitation light emitted by the first light source has an excitation waveband of $\lambda_{ex} \pm \Delta\lambda_{ex}$.

3. The system of claim 2, wherein the sensor is configured such that a registered image is defined by an emission waveband $\lambda_{em} \pm \Delta\lambda_{em}$, and wherein $\lambda_{em} \pm \Delta\lambda_{em} \neq \lambda_{ex} \pm \Delta\lambda_{ex}$.

4. The system of claim 1, wherein the first light source is a broadband emitting light source with at least one filter applied to for generating an excitation waveband of $\lambda_{ex} \pm \Delta\lambda_{ex}$.

5. The system of claim 4, wherein at least one optical filter is arranged in front of the sensor so that only filtered light of the emission waveband $\lambda_{em} \pm \Delta\lambda_{em}$ reaches the sensor.

6. The system of claim 4, wherein the sensor is insensitive to the excitation waveband of $\lambda_{ex} \pm \Delta\lambda_{ex}$ and sensitive to at least a portion of the emission waveband $\lambda_{em} \pm \Delta\lambda_{em}$.

7. The system of claim 1, wherein the sensor is a time delay integration line scan camera.

8. The system of claim 1, wherein the first excitation light emitted by the first light source travels through the optical unit to the layer with photo luminescent properties.

9. The system of claim 1, wherein the first excitation light emitted by the first light source travels outside the optical unit to the layer with photo luminescent properties.

10. The system of claim 1, further comprising a second light source emitting second excitation light, wherein:
the first excitation light emitted by the first light source travels through the optical unit to the layer with photo luminescent properties; and,
the second excitation light emitted by the second light source travels outside the optical unit to the layer with photo luminescent properties.

11. The system of claim 1, wherein the first light source is a lamp or a combination of lamps.

12. The system of claim 1, wherein the first light source is an LED or a combination of LEDs.

13. The system of claim 1, wherein the first light source is a laser or a combination of lasers.

14. The system of claim 1, wherein the optical unit has a microscope objective and at least one optical filter so that only light with an emission waveband of $\lambda_{em} \pm \Delta\lambda_{em}$ from the layer with photo luminescent properties reaches the sensor.

15. The system of claim 14, wherein the microscope objective defines a beam path, and a dichroic beam splitter is arranged in the optical unit such that light from the at least one first light source with the excitation waveband of $\lambda_{ex} \pm \Delta\lambda_{ex}$ is coupled into the beam path of the microscope objective.

16. The system of claim 14, wherein the microscope objective defines a first beam path, and light from a second light source with the excitation waveband of $\lambda_{ex} \pm \Delta\lambda_{ex}$ defines an illumination beam path different from the first beam path of the microscope objective.

17. The system of claim 14, wherein:
the microscope objective defines a first beam path;
a dichroic beam splitter is arranged in the optical unit such that light of the excitation waveband of $\lambda_{ex} \pm \Delta\lambda_{ex}$ is coupled into the first beam path of the microscope objective; and,
light from a second light source with the excitation waveband of $\lambda_{ex} \pm \Delta\lambda_{ex}$ defines an illumination beam path different from the first beam path of the microscope objective.

18. The system of claim 1, wherein the layer with photo luminescent properties is composed of a bulk material with photo luminescent properties coated with a reflective material.

19. The system of claim 1, wherein the layer with photo luminescent properties is composed of a transparent bulk material coated with a second material with photo luminescent properties which is coated with a reflective material.

20. A system for back light inspection of a transparent or semitransparent object, comprising:
an object carrier with a carrier base and a layer with photo luminescent properties;
a first light source arranged above the object carrier such that first excitation light emitted from the first light source is directed through the transparent or semitransparent object to the layer with photo luminescent properties;
an optical unit adapted to capture emission light emitted from the layer with photo luminescent properties and traveled through the transparent or semitransparent object; and
a sensor for registering the emission light captured by the optical unit,
wherein the object carrier is arranged to move the transparent or semitransparent object.

* * * * *